United States Patent [19]

Weithmann et al.

[11] Patent Number: 4,850,489
[45] Date of Patent: Jul. 25, 1989

[54] DISPENSING PACKS CONTAINING PHARMACEUTICAL COMBINATIONS FOR SEQUENTIAL ADMINISTRATION

[75] Inventors: Klaus U. Weithmann, Hofheim am Taunus; Dirk Seiffge, Münzenberg, both of Fed. Rep. of Germany

[73] Assignee: Hoechst Aktiengesellschaft, Fed. Rep. of Germany

[21] Appl. No.: 287,601

[22] Filed: Dec. 22, 1988

Related U.S. Application Data

[63] Continuation of Ser. No. 71,425, Jul. 9, 1987, abandoned.

[30] Foreign Application Priority Data

Jul. 11, 1986 [DE] Fed. Rep. of Germany ....... 3623331

[51] Int. Cl.⁴ .............................................. B65D 83/04
[52] U.S. Cl. .................................... 206/530; 206/528; 206/538; 424/464
[58] Field of Search ............... 206/530, 532, 535, 538, 206/539, 528; 424/467, 464

[56] References Cited

U.S. PATENT DOCUMENTS

| 462,990 | 11/1891 | Oppenheimer | 206/538 |
|---|---|---|---|
| 2,317,860 | 4/1943 | Sorensen | 206/42 |
| 2,777,570 | 1/1957 | Mytinger | 206/539 |
| 3,207,299 | 9/1965 | Sparks | 206/532 |
| 3,236,369 | 2/1966 | Moore | 206/539 |
| 3,689,458 | 9/1972 | Hellstrom | 206/530 |
| 4,039,080 | 8/1977 | Cappuccilli | 206/538 |
| 4,371,080 | 2/1983 | Haines | 206/532 |
| 4,553,670 | 11/1985 | Collens | 206/534 |
| 4,693,371 | 9/1987 | Malpass | 206/538 |

FOREIGN PATENT DOCUMENTS

| 1884978 | 9/1963 | Fed. Rep. of Germany . |
|---|---|---|
| 1952900 | 4/1966 | Fed. Rep. of Germany . |
| 7019777 | 8/1970 | Fed. Rep. of Germany . |
| 2834226 | 2/1980 | Fed. Rep. of Germany . |
| 3515874 | 1/1986 | Fed. Rep. of Germany . |
| 2368280 | 5/1978 | France . |
| 855458 | 7/1985 | South Africa . |
| 1073786 | 3/1965 | United Kingdom . |
| 2105988 | 4/1983 | United Kingdom . |

OTHER PUBLICATIONS

P. H. List, L. Horhammer in Hagers Handbuch der Pharmazeutischen Praxis, 1971, pp. 690–691.

Primary Examiner—David T. Fidei
Attorney, Agent, or Firm—Finnegan, Henderson, Farabow, Garrett & Dunner

[57] ABSTRACT

Dispensing packs which contain chambers with at least two solid, not mechanically connected dosage units of various pharmaceuticals.

11 Claims, 1 Drawing Sheet

DISPENSING PACKS CONTAINING PHARMACEUTICAL COMBINATIONS FOR SEQUENTIAL ADMINISTRATION

BACKGROUND OF THE INVENTION

In many cases, the physician will prescribe that a patient take several pharmaceuticals, and specifically in such a way that the pharmaceuticals are to be taken simultaneously or at intervals. Boxes have been developed for this purpose in hospitals for their own use, in which boxes the totality of the pharmaceuticals for one day is supplied to the patient all at once. The possibilities of error in intake are not ruled out by this, since it is always possible for the patient to forget to take one or other of the tablets, or not to comply with the prescribed time interval.

It has also emerged that, in certain cases, consecutive administration of two pharmacological active compounds at intervals results in surprising and exceptional effects, that is to say this entails one component being released first. Thus, sequential consecutive administration of (A) xanthine derivatives or their active metabolites on the one hand, and (B) acetylsalicylic acid or its pharmacologically tolerated salts on the other hand, in a particular sequence, brings about an extremely large improvement in the therapy of diseases which are caused by or associated with derangements of the constituents of blood, especially platelets and erythrocytes, but also leukocytes. The sequential administration of xanthine derivatives, especially pentoxifylline, which is followed after a minimum of 10 minutes to 4 hours by administration of acetylsalicylic acid or its salt, results in much more potent effects than when the combination of the two individual substances is administered at once, in which case there is in fact a reduction in this action.

Dispensing packs which contain various chambers and, in addition, adjacent thereto instructions for intake have already been described (U.S. Pat. No. 4,553,670). Although it is possible by use of these dispensing packs to reduce errors by the patient with regard to correct timing of intake, it is not possible to rule them out. Where dispensing packs of this type contained more than one dosage unit, the units were identical in form. Moreover, it is not possible by use of dispensing packs of this type to avoid abrasion damage to the two dosage units during movements of the pack, which are unavoidable.

The invention thus has the object of even further increasing the security against mix-ups for the patient where administration of several tablets is necessary and can be predicted beforehand by the manufacturer of pharmaceuticals.

DESCRIPTION OF THE INVENTION

Thus the present invention relates to dispensing packs which contain chambers with at least two solid, not mechanically connected dosage units of various pharmaceuticals which preferably differ recognizably from one another, for example in their size, weight, shape and/or color. Where it is necessary for release in the body to take place at intervals, one pharmaceutical can be in a delayed release form. A preferred embodiment comprises the various dosage units also being mechanically separated from one another by the spatial configuration of the chambers, preferably a ridge-like arching (1) (see FIG. 8), and being so tightly secured that the spatial separation is ensured and no abrasion damage takes place.

Although the term "various pharmaceuticals" particularly designates those which contain various active compounds, it is also intended to embrace combinations which although containing the same active compound contain it in various separate delivery forms, for example in immediate release and delayed release forms.

A preferred embodiment provides dispensing packs which contain, side by side, solid dosage units of, in each case, (A) a xanthine derivative of the formula I or II (see claim 8) or prodrugs of oxoalkyl- or hydroxyalkylxanthines, or their active metabolites on the one hand, and (B) O-acetylsalicylic acid or its pharmacologically tolerated salts, the component B being present in delayed release form, and each of the two components (A) and (B) preferably being processed with a pharmaceutical vehicle. In formula I one of the radicals $R^1$ and $R^3$ is a straight-chain alkyl, $(\omega\text{-1})$-oxoalkyl or $(\omega\text{-1})$-hydroxyalkyl group having 3 to 8 carbon atoms, and the two other radicals $R^2$ and $R^3$, or $R^1$ and $R^2$, represent straight-chain or branched alkyl groups having 1 to 8 carbon atoms in the position of $R^1$ and $R^3$, and 1 to 4 carbon atoms in the position of $R^2$, the total of the carbon atoms in these two alkyl substituents not exceeding 10, and in formula II R is an alkyl radical having 1 to 4 carbon atoms. In this context, the xanthine compounds of the formula I which are preferably present are those in which $R^1$ or $R^3$ denotes an alkyl, $(\omega\text{-1})$-oxoalkyl or $(\omega\text{-1})$-hydroxyalkyl radical having 5 or 6 carbon atoms, and the two alkyl substituents $R^2$ and $R^3$, or $R^1$ and $R^2$, together comprise 2 to 6 carbon atoms. Those of the latter which are in turn preferred are those in which a hexyl, 5-oxohexyl or 5-hydroxyhexyl group is located in the position of $R^1$ or $R^3$, and, in particular, 1-hexyl-3,7-dimethylxanthine, 1-(5-hydroxyhexyl)-3,7-dimethylxanthine, 1-(5-oxohexyl)-3,7-dimethylxanthine, 1,3-dimethyl-7-(5-hydroxyhexyl)xanthine, 1,3-dimethyl-7-(5-oxohexyl)xanthine, 1-(5-hydroxyhexyl)-3-methyl-7-propylxanthine or 1-(5-oxohexyl)-3-methyl-7-propylxanthine.

The xanthine derivative can also be present in prodrug form as acetalized oxoalkylxanthine, in which at least one carbonyl group is replaced by the structural element of the formula

(III)

or as O-acylated hydroxyalkylxanthine having the structural element of the formula $R^6\text{---CO---O---}$ (IV), $R^4$ and $R^5$ each representing an alkyl group having up to 4 carbon atoms, or together representing an ethylene, trimethylene or tetramethylene group, and $R^6$ denoting an alkyl radical having up to 4 carbon atoms, phenyl, substituted phenyl, pyridyl or substituted pyridyl.

Dispensing packs of this type are very particularly suitable for agents, which, by reason of their superadditive effects, are intended for antithrombotic, bloodflow-promoting, antiinflammatory, analgesic, antiaggregatory and cytostatic therapy or prophylaxis. Because of the superadditive effect on delayed release, it is possible for the amounts of, for example, xanthine derivative and acetylsalicylic acid to be administered to be reduced to those amounts which, on administration thereof alone, show an only minimal pharmacological action, so that, at the same time, side effects caused by high doses of these active compounds are reduced. This is of great importance because, as is known, acetylsalicylic acid in the customary dosages may cause undesired side effects such as asthma, allergic urticaria, analgesic nephropathy and gastrointestinal ulcers. Thus the invention makes it possible safely to dose these two active compounds in the requisite manner, that is to say to rule out faulty dosages.

In analogy to combinations of xanthine derivatives and acetylsalicylic acid, it is also possible according to the invention to provide those of (A) pyrimidopyrimidines of the formula IV, such as dipyridamole—cf. German Offenlegungsschrift No. 3,515,874—with (B) O-acetylsalicylic acid or its pharmaceutically tolerated salts for the same indication. In formula IV at least one of the radicals $R^6$ and $R^8$ represents the radical —N(CH$_2$—CHR$^{10}$—OH)$_2$, with $R^{10}$=hydrogen or methyl, and at least one of the radicals $R^7$ and $R^9$ represents the radical

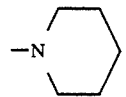

which can also be interrupted by oxygen in the p-position to the nitrogen atom. Instead of this, it is also possible for an active metabolite and/or an active salt to be present. In this context, the ratio by weight of component (A) to component (B) should be greater than 0.5. These two components can be processed with or without (C) a pharmaceutical vehicle. Combinations of this type are likewise used for sequential administration in the therapy of diseases which are caused by or associated with derangements of blood functions or blood constituents, especially platelets and erythrocytes, the intention being that component (A) is released first.

Thus the invention makes it possible successfully to design therapy with combinations of several substances, in that the patient reliably, i.e. simultaneously, takes the components of this pharmaceutical combination, it also being possible, for example by incorporation of agents for delaying release in a pharmaceutical, for a chronological relationship to be set up between the actions of the various pharmaceuticals.

Figure 1:
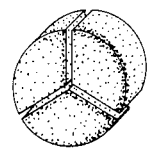
FIGS. 1–7 are directed to various geometrical shapes of dispensing packs.
Figure 2:
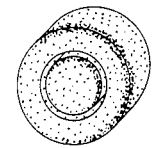
Figure 3:
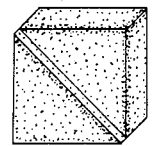
Figure 4:
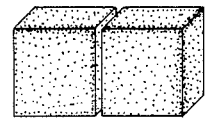
Figure 5:
Figure 6:
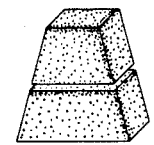
Figure 7:
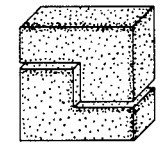
Figure 8:
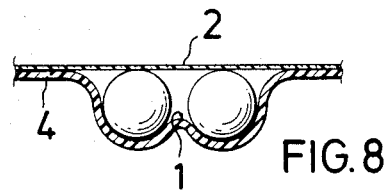
FIGS. 8 and 9 are frontal views of various blister packs.
Figure 9:
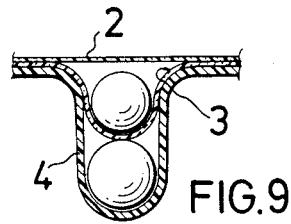

Views of some of the configurational shapes, some of which have not been customary hitherto, of the combinations according to the invention are depicted in FIGS. 1 to 9. The shapes of the individual dosage units are preferably such that they have a geometrically (stereometrically) symmetrical shape either alone or in combination with one another, for example the customary tablet shape or spherical, cylindrical, disk, rod, ellipsoidal, conical, biconical or truncated biconical shape, or are a combination of disk and ring. Thus, according to another preferred embodiment, it is possible to increase the security against mix-ups on intake by supplying the individual dosage units as parts of geometric (stereometric) shapes, for example as two hemispheres which are identical in size but arranged as mirror images and, for example, of different colors or, in a multicomponent system, as segments of a sphere. It is particularly advantageous if the characteristics of the parts are such that they can be fitted together (lock and key principle, see FIGS. 5 and 7).

It is also possible to attain good security against mix-ups on intake when the dosage units, for example in a blister pack, are arranged in such a way that they can be removed simultaneously, for example are located in a common chamber (see FIG. 8), and are possibly supplied in the form of cylinders or hemispheres or as combination (see, for example, FIGS. 1 to 7). It is also possible to use, for the spatial separation of the dosage units, sheets (3) in addition to the sheets (2) and (4) used to manufacture the blister packs (see FIGS. 8 and 9).

What is claimed is:

1. A package for the dispensing of pharmaceutical compounds comprising at least one chamber, said chamber containing at least two solid drugs of different compounds, said drugs not mechanically connected to one another and being arranged to form a combined geometrical shape and said drugs being individually separable from one another for sequential administration whereby administration of at least one of said drugs alters the combined geometrical shape thereby readily indicating the remainder of said drugs to be administered.

2. A dispensing package as in claim 1, wherein said drugs differ from one another in their color.

3. A dispensing package as in claim 1, comprising a plurality of chambers containing said drugs, said drugs are mechanically separated from one another by a spatial configuration of said chambers.

4. A dispensing package as in claim 1, wherein said package is a blister pack comprising a plurality of chambers, each chamber containing said drugs and separated from one another by an additional sheet.

5. A dispensing package as claimed in claim 1, which contains solid dosage units of:

(A) a xanthine derivative of the formula (I) or (II)

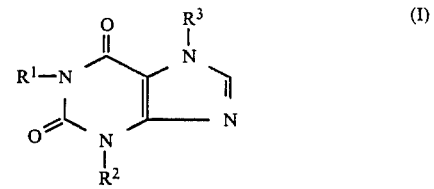

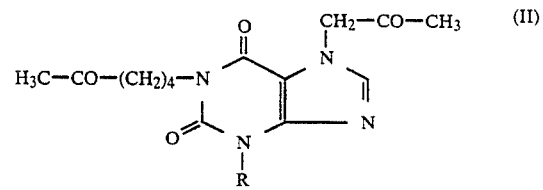

or prodrugs of oxoalkyl- or hydroxyalkylxanthines, or their active metabolites, wherein in formula I one of the radicals $R^1$ and $R^3$ is a straight-chain alkyl, ($\omega$-1)-oxoalkyl or ($\omega$−1)-hydroxyalkyl radical having 3 to 8 carbon atoms, and the two other radicals $R^2$ and $R^3$, or $R^1$ and $R^2$, are straight-chain or branched alkyl radicals having 1 to 8 carbon atoms in the positions of $R^1$ and $R^3$, and having 1 to 4 carbon atoms in the position of $R^2$, the total of the carbon atoms in said two other radicals not exceeding 10, and in formula II, R is an alkyl radical having 1 to 4 carbon atoms, and (B) O-acetylsalicylic acid or a pharmacologically tolerated salt thereof present in delayed release form.

6. A dispensing package as claimed in claim 5 wherein each of the two components (A) and (B) is processed with a pharmaceutical vehicle.

7. A dispensing package is claimed in claim 1, which contains solid dosage units of:

(A) a pyrimidopyrimidine of the formula IV

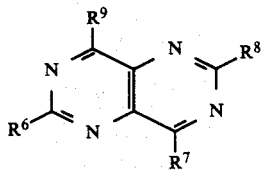

(IV)

in which at least one of the radicals $R^6$ and $R^8$ is the radical $-N(CH_2-CHR^{10}-OH)_2$ wherein $R^{10}$ is hydrogen or methyl, and at least one of the radicals $R^7$ and $R^9$ is the radical

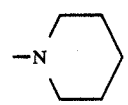

or an active metabolic or salt thereof, and (B) O-acetylsalicylic acid or a pharmaceutically tolerated salt thereof, the ratio by weight of component (A) to component (B) being greater than 0.5.

8. A dispensing package as claimed in claim 7, wherein the radical

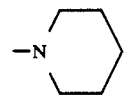

is interrupted by oxygen in the para position to the nitrogen atom.

9. A dispensing package as claimed in claim 8 wherein each of the components (A) and (B) is processed with a pharmaceutical vehicle.

10. A dispensing package as claimed in claim 7 wherein each of the components (A) and (B) is processed with a pharmaceutical vehicle.

11. A dispensing package as claimed in claim 1 wherein said not mechanically connected dosage units have in combination with one another a spherical, cylindrical, disk, rod, ellipsoidal, conical, biconical or truncated biconical geometrically symmetrical shape, or are a combination of disk and ring.

* * * * *